(12) United States Patent
Song et al.

(10) Patent No.: US 7,094,528 B2
(45) Date of Patent: Aug. 22, 2006

(54) MAGNETIC ENZYME DETECTION TECHNIQUES

(75) Inventors: Xuedong Song, Roswell, GA (US); Shu-Ping Yang, Alpharetta, GA (US); Rosann Marie Matthews Kaylor, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/881,316

(22) Filed: Jun. 30, 2004

(65) Prior Publication Data

US 2006/0057661 A1    Mar. 16, 2006

(51) Int. Cl.
    *C12Q 1/00* (2006.01)
(52) U.S. Cl. ............... 435/4; 435/18; 435/23; 435/24; 435/287.7; 435/173.2
(58) Field of Classification Search ............ 435/4, 435/18, 23, 24, 173.2, 287.7; 434/287.7
    See application file for complete search history.

(56) References Cited

U.S. PATENT DOCUMENTS

| | | | |
|---|---|---|---|
| 4,275,149 A | 6/1981 | Litman et al. | |
| 4,477,635 A | 10/1984 | Mitra | |
| 4,614,723 A | 9/1986 | Schmidt et al. | |
| 4,748,116 A | 5/1988 | Simonsson et al. | |
| 4,962,024 A | 10/1990 | Schulte | |
| 5,075,077 A | 12/1991 | Durley, III et al. | |
| 5,124,254 A | 6/1992 | Hewlins et al. | |
| 5,200,084 A | 4/1993 | Liberti et al. | |
| 5,252,459 A | 10/1993 | Tarcha et al. | |
| 5,292,652 A | 3/1994 | Dovey et al. | |
| 5,464,741 A | 11/1995 | Hendrix | |
| 5,466,574 A | 11/1995 | Liberti et al. | |
| 5,514,785 A | 5/1996 | Van Ness et al. | |
| 5,518,883 A | 5/1996 | Soini | |
| 5,573,909 A | 11/1996 | Singer et al. | |
| 5,585,273 A | 12/1996 | Lawrence et al. | |
| 5,585,279 A | 12/1996 | Davidson | |
| 5,591,581 A | 1/1997 | Massey et al. | |
| 5,637,509 A | 6/1997 | Hemmilä et al. | |
| 5,647,994 A | 7/1997 | Tuunanen et al. | |
| 5,670,381 A | 9/1997 | Jou et al. | |
| 5,700,636 A | 12/1997 | Sheiness et al. | |
| 5,731,147 A | 3/1998 | Bard et al. | |
| 5,786,137 A | 7/1998 | Diamond et al. | |
| 5,795,470 A | 8/1998 | Wang et al. | |
| 5,837,429 A | 11/1998 | Nohr et al. | |
| 5,866,434 A * | 2/1999 | Massey et al. ............ 436/526 |
| 5,872,261 A | 2/1999 | Bremmer et al. | |
| 5,876,944 A | 3/1999 | Kuo | |
| 5,922,537 A | 7/1999 | Ewart et al. | |
| 5,932,410 A | 8/1999 | Whittaker et al. | |
| 5,981,207 A | 11/1999 | Burbaum et al. | |
| 6,004,530 A | 12/1999 | Sagner et al. | |
| 6,030,840 A | 2/2000 | Mullinax et al. | |
| 6,033,574 A | 3/2000 | Siddiqi | |
| 6,136,549 A * | 10/2000 | Feistel ............ 435/7.1 |
| 6,174,646 B1 | 1/2001 | Hirai et al. | |
| 6,197,537 B1 | 3/2001 | Rao et al. | |
| 6,235,464 B1 | 5/2001 | Henderson et al. | |
| 6,242,268 B1 | 6/2001 | Wieder et al. | |
| 6,243,980 B1 | 6/2001 | Bronstein et al. | |
| 6,251,621 B1 | 6/2001 | Lawrence et al. | |
| 6,261,779 B1 | 7/2001 | Barbera-Guillem et al. | |
| 6,287,798 B1 | 9/2001 | James et al. | |
| 6,306,665 B1 | 10/2001 | Buck et al. | |
| 6,348,319 B1 | 2/2002 | Braach-Maksvytis et al. | |
| 6,362,011 B1 | 3/2002 | Massey et al. | |
| 6,387,707 B1 | 5/2002 | Seul et al. | |
| 6,444,423 B1 | 9/2002 | Meade et al. | |
| 6,451,619 B1 | 9/2002 | Catt et al. | |
| 6,468,741 B1 | 10/2002 | Massey et al. | |
| 6,485,926 B1 | 11/2002 | Nemori et al. | |
| 6,562,631 B1 | 5/2003 | Braach-Maksvytis et al. | |
| 6,582,930 B1 | 6/2003 | Ponomarev et al. | |
| 6,585,939 B1 | 7/2003 | Dapprich | |
| 6,613,583 B1 | 9/2003 | Richter et al. | |
| 6,682,903 B1 | 1/2004 | Saunders | |
| 6,720,007 B1 | 4/2004 | Walt et al. | |

(Continued)

FOREIGN PATENT DOCUMENTS

EP    0244932 A2    11/1987

(Continued)

OTHER PUBLICATIONS

The Random House College Dictionary, Revised Edition. "Magnetic". Random House, Inc., 1980, p. 805.*

(Continued)

*Primary Examiner*—Francisco C. Prats
*Assistant Examiner*—Susan E. Fernandez
(74) *Attorney, Agent, or Firm*—Dority & Manning, P.A.

(57) ABSTRACT

A diagnostic test kit for detecting the presence or quantity of an enzyme or enzyme inhibitor is provided. The diagnostic kit utilizes reactive complexes to facilitate the detection of the enzyme or enzyme inhibitor. The reactive complexes include a substrate joined (e.g., covalently bonded, physically adsorbed, etc.) to a reporter and magnetic substance. In one embodiment, for example, a peptide, protein, or glycoprotein substrate is joined to a reporter (e.g., dyed latex particle) and magnetic particle. In this embodiment, the substrate provides a cleavage target for a proteolytic enzyme. Specifically, upon contacting the reactive complexes, the proteolytic enzyme cleaves the substrate and releases the reporter and/or magnetic particle. The signal exhibited by the released reporters may then be used to indicate the presence or quantity of an enzyme or enzyme inhibitor within the test sample.

22 Claims, 6 Drawing Sheets

U.S. PATENT DOCUMENTS

| | | |
|---|---|---|
| 2002/0025541 A1 | 2/2002 | Nelson et al. |
| 2003/0119202 A1 | 6/2003 | Kaylor et al. |
| 2003/0124739 A1 | 7/2003 | Song et al. |
| 2004/0014073 A1 | 1/2004 | Trau et al. |
| 2004/0043502 A1 | 3/2004 | Song et al. |
| 2004/0043507 A1 | 3/2004 | Song et al. |
| 2004/0043511 A1 | 3/2004 | Song et al. |
| 2004/0043512 A1 | 3/2004 | Song et al. |
| 2004/0081971 A1 | 4/2004 | Yue et al. |
| 2004/0096918 A1 | 5/2004 | Martin et al. |
| 2004/0121480 A1 | 6/2004 | Wei et al. |

FOREIGN PATENT DOCUMENTS

| | | |
|---|---|---|
| EP | 0244932 A3 | 11/1987 |
| EP | 0297290 A2 | 1/1989 |
| EP | 1422525 A1 | 5/2004 |
| WO | WO 8804777 A1 | 6/1988 |
| WO | WO 9743438 A1 * | 11/1997 |
| WO | WP 9964864 A1 | 12/1999 |
| WO | WO 0163299 A1 | 8/2001 |
| WO | WO 03085403 A1 | 10/2003 |
| WO | WO 2005066359 A1 | 7/2005 |

OTHER PUBLICATIONS

Gan, Z et al. Protease and protease inhibitor assays using biotinylated casein coated on a solid phase. Analytical Biochemistry. 1999. 268: 151-156.*

"Mass Properties and Susceptibilities Chart" (http://www.reade.com/Particle-Briefings/magnetic_susceptibilities.html, copyright 1997, accessed Aug. 9, 2005).*

Abstract of DE 10024145A1, Nov. 22, 2001.

Article—*Solid Substrate Phosphorescent. Immunoassay Based On Bioconjugated Nanopartricles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

U.S. Appl. No. 10/882,108, filed Jun. 30, 2004, Song, Enzymatic Detection Techniques.

U.S. Appl. No. 10/881,010, filed Jun. 20, 2004, Song, One-step Enzymatic And Amine Detection Technique.

Abstract of Article entitled *One-step all-in-one dry reagent immunoassays with fluorescent europium chelate label and time-resolved fluorometry*, T. Lovgren, L. Merio, K. Mitrunen, M. L. Makinen, M. Makela, K. Blomberg, T. Palenius, and K. Pettersson, Clinical Chemistry, vol. 42, 1996, pp. 1196-1201.

Article—*Effect of matrix metalloprotease inhibitors on the 95 kDa metallopeptidase of Candida albicans*, C. Imbert, C. Knauffmann-Lacroix, G. Daniault, J. L. Jacquemin, and M. H. Rodier, Journal of Antimicrobial Chemotherapy, vol. 99, 2002, pp. 1007-1010.

Paper—Section 10.4—Detecting Peptidases and Proteases, 19 pages, www.probes.com/handbook.

Product Description for BioMag® Carboxyl-terminated Particles from Bangs Laboratories, Inc. 2 pages.

Product Description for EnzChek™ Protease Assay Kits from Molecular Probes, 3 pages.

Product Description for EZ-Link NHS-PEO Solid Phase Biotinylation Kit from Pierce, 4 pages.

Product Description for EZ-Link® Sulfo-NHS-Biotin Reagents from Pierce, 5 pages.

Product Description for Fluorescence Microplate Assays from Molecular Probes, 112 pages.

Product Information on Enzymatic Assay of PROTEASE[1] Casein as a Substrate from Sigma, 4 pages.

Search Report and Written Opinion for PCT/US2005/011051, Sep. 9, 2005.

Search Report and Written Opinion for PCT/US2005/01105o, Sep. 19, 2005.

Search Report and Written Opinion for PCT/US2005/014169, Nov. 4, 2005.

* cited by examiner

MAGNETIC ENZYME DETECTION TECHNIQUES

BACKGROUND OF THE INVENTION

It is often desirable to determine the presence or quantity of a particular enzyme within a test sample. In some cases, the mere presence of an enzyme may, for example, indicate the existence of tissue or organ damage. Likewise, abnormal enzyme concentrations may also indicate other conditions, such as a bacterial or viral infection. For instance, proteases (e.g., aspartic proteases) and metallopeptidases are believed to increase the pathogenicity of *Candida albicans*, a microorganism that may cause candidal vaginitis ("yeast infection"). The presence or concentration of an enzyme in a test sample may also serve as a diagnostic marker for some types of cancers and other conditions. For instance, prostate-specific antigen (PSA) is a well-known marker for prostate cancer. Other examples of diagnostic markers include cathepsin B (cancer), cathepsin G (emphysema, rheumatoid arthritis, inflammation), plasminogen activator (thrombosis, chronic inflammation, cancer), and urokinase (cancer).

One conventional technique for detecting the presence of an enzyme is described in U.S. Pat. No. 6,348,319 to Braach-Maksvytis, et al. Braach-Maksvytis, et al. functions by sensing the digestion of a substrate by the enzyme. For example, FIG. 1 of Braach-Maksvytis, et al. illustrates a device 10 that includes a first zone 11 and a second zone 12. The first zone 11 is provided with polymer beads 13 (carrier) linked to streptavidin 14 (probe) via a peptide linker 15 that is cleavable by a protease 16. Upon addition of the protease 16, the streptavidin 14 is released and passes to the second zone 12, which includes a biosensor membrane 17 that detects the presence of streptavidin through a change in the impedance of the membrane. (Col. 5, ll. 25–30). Unfortunately, however, techniques such as described by Braach-Maksvytis, et al., are far too complex and cost prohibitive for certain types of applications, such as those requiring a relatively quick diagnosis by a patient (self-diagnosis or with the aid of medical personnel).

As such, a need currently exists for a simple and inexpensive technique to accurately detect the presence of an enzyme within a test sample.

SUMMARY OF THE INVENTION

In accordance with one embodiment of the present invention, a method for detecting an enzyme, or an inhibitor thereof, within a test sample, is disclosed. The method comprises contacting a test sample with a plurality of reactive complexes to form an incubation mixture. The reactive complexes each comprise a substrate joined to a reporter and magnetic substance. The substrate is cleavable by an enzyme to release the reporter, the released reporter being capable of directly or indirectly generating a detection signal. The incubation mixture is subjected to a magnetic field to separate a first portion containing the magnetic substance from a second portion. The presence or intensity of a detection signal is determined. In some embodiments, the method further comprises contacting the second portion with probes conjugated with a specific binding member, the probes further comprising a detectable substance that is capable of directly generating the detection signal. If desired, an assay (e.g., competitive or sandwich immunoassays) may also be employed to determine the presence or concentration of the released reporters within the second portion.

In accordance with another embodiment of the present invention, a diagnostic test kit for detecting an enzyme, or an inhibitor thereof, within a test sample, is disclosed. The kit comprises a plurality of reactive complexes that each comprises a substrate joined to a reporter and magnetic particle, wherein the substrate is cleavable by an enzyme to release the reporter, the released reporter being capable of directly or indirectly generating a detection signal. In one embodiment, the second portion may be assayed using a chromatographic medium that defines a first detection zone within which the detection signal is capable of being generated. For example, a first receptive material may be immobilized within the first detection zone that is capable of binding to the released reporter or complexes thereof. In addition, the chromatographic medium may further comprise a second detection zone within which a second detection signal is capable of being generated. For example, a second receptive material may be immobilized within the second detection zone that is capable of binding to probes or complexes thereof, wherein the probes comprise a detectable substance capable of directly generating the second detection signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
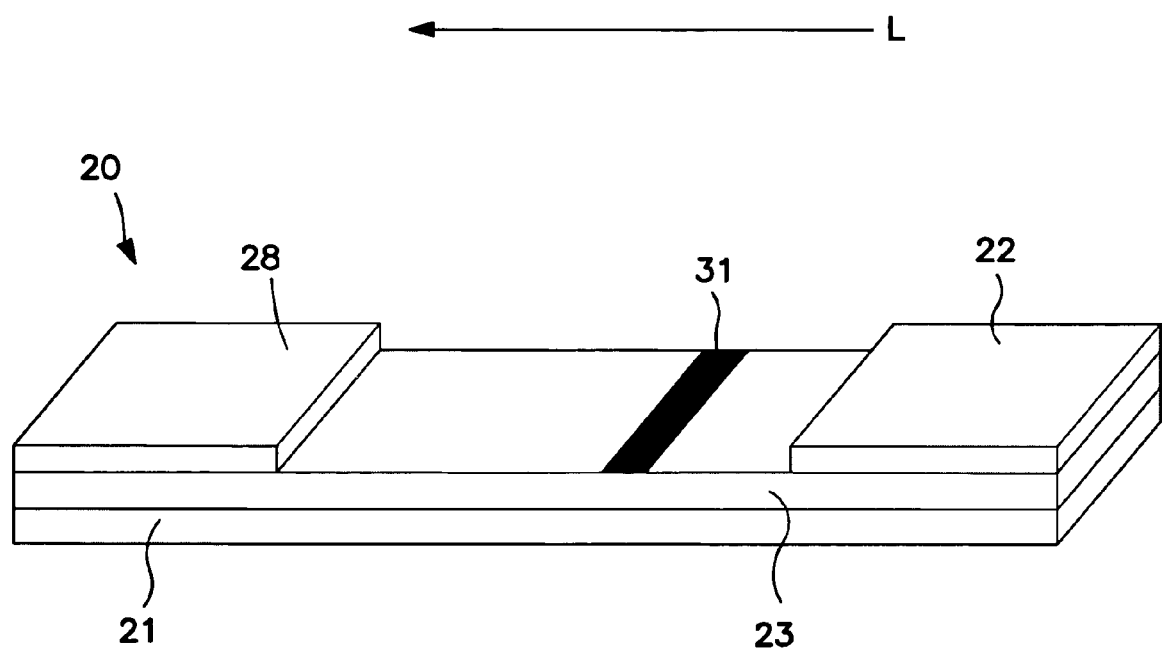
FIG. 1 is a perspective view of one embodiment of an assay device that may be used in the diagnostic test kit of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "test sample" generally refers to a material suspected of containing an enzyme and/or enzyme inhibitor. For example, the test sample may be obtained or derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid, and so forth. Besides physiological fluids, other liquid samples may be used such as water, food products, and so forth, for the performance of environmental or food production assays. In addition, a solid material may be used as the test sample. The test sample may be used directly as obtained from a source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, etc. Moreover, it may also be beneficial to modify a solid test sample to form a liquid medium, to release the enzyme and/or enzyme inhibitor, etc.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention is generally directed to a diagnostic test kit for detecting the presence or quantity of an enzyme or enzyme inhibitor. The diagnostic kit utilizes reactive complexes to facilitate the detection of the enzyme or enzyme inhibitor. The reactive complexes include a substrate joined (e.g., covalently bonded, physically adsorbed, etc.) to a reporter and magnetic substance. In one embodiment, for example, a peptide, protein, or glycoprotein substrate is joined to a reporter (e.g., dyed latex particle) and magnetic particle. In this embodiment, the substrate provides a cleavage target for a proteolytic enzyme. Specifically, upon contacting the reactive complexes, the proteolytic enzyme cleaves the substrate and releases the reporter and/or magnetic particle. The signal exhibited by the released reporters may then be used to indicate the presence or quantity of an enzyme or enzyme inhibitor within the test sample.

Various types of enzymes may be detected in accordance with the present invention. For instance, transferases, hydrolases, lyases, and so forth, may be detected. In some embodiments, the enzyme of interest is a "hydrolase" or "hydrolytic enzyme", which refers to enzymes that catalyze hydrolytic reactions. Examples of such hydrolytic enzymes include, but are not limited to, proteases, peptidases, lipases, nucleases, homo- or hetero-oligosaccharidases, homo- or hetero-polysaccharidases, phosphatases, sulfatases, neuraminidases and esterases. In one embodiment, for example, peptidases may be detected. "Peptidases" are hydrolytic enzymes that cleave peptide bonds found in shorter peptides. Examples of peptidases include, but are not limited to, metallopeptidases; dipeptidylpeptidase I, II, or IV; and so forth. In another embodiment, proteases may be detected. "Proteases" are hydrolytic enzymes that cleave peptide bonds found in longer peptides and proteins. Examples of proteases that may be detected according to the present invention include, but are not limited to, serine proteases (e.g., chymotrypsin, trypsin, elastase, PSA, etc.), aspartic proteases (e.g., pepsin), thiol proteases (e.g., prohormone thiol proteases), metalloproteases, acid proteases, and alkaline proteases. Still other enzymes are described in U.S. Pat. No. 6,243,980 to Bronstein, et al. and 2004/0081971 to Yue, et al., which are incorporated herein in their entirety by reference thereto for all purposes.

Likewise, any of a variety of known enzyme inhibitors may also be detected in accordance with the present invention. For example, known inhibitors of hydrolytic enzymes include, but are not limited to, inhibitors of proteases, peptidases, lipases, nucleases, homo- or hetero-oligosaccharidases, homo- or hetero-polysaccharidases, phosphatases, sulfatases, neuraminidases and esterases. Protease inhibitors may include, for instance, aspartic protease inhibitors, serine protease inhibitors, thiol protease inhibitors, metalloprotease inhibitors, acid or alkaline protease inhibitors, and so forth. Some specific examples of protease inhibitors include benzamideine, indole, pepstatin, ovomacroglobulin, haloperidol, transition state mimetics, and so forth.

As stated above, reactive complexes are used in the present invention to detect the presence or quantity of an enzyme or enzyme inhibitor. The reactive complexes include a substrate joined to a reporter and specific binding member. The term "substrate" generally refers to a substance that is chemically acted upon by an enzyme to form a product. The substrate may occur naturally or be synthetic. Some suitable substrates for hydrolytic enzymes include, for instance, esters, amides, peptides, ethers, or other chemical compounds having an enzymatically-hydrolyzable bond. The enzyme-catalyzed hydrolysis reaction may, for example, result in a hydroxyl or amine compound as one product, and a free phosphate, acetate, etc., as a second product. Specific types of substrates may include, for instance, proteins or glycoproteins, peptides, nucleic acids (e.g., DNA and RNA), carbohydrates, lipids, esters, derivatives thereof, and so forth. For instance, some suitable substrates for peptidases and/or proteases may include peptides, proteins, and/or glycoproteins, such as casein (e.g., β-casein, azocasein, etc.), albumin (e.g., bovine serum albumin (BSA)), hemoglobin, myoglobin, keratin, gelatin, insulin, proteoglycan, fibronectin, laminin, collagen, elastin, and so forth. Still other suitable substrates are described in U.S. Pat. No. 4,748,116 to Simonsson, et al.; U.S. Pat. No. 5,786,137 to Diamond, et al.; U.S. Pat. No. 6,197,537 to Rao, et al.; and U.S. Pat. No. 6,235,464 to Henderson, et al.; U.S. Pat. No. 6,485,926 to Nemori, et al., which are incorporated herein in their entirety by reference thereto for all purposes.

The reporters may contain any substance capable of directly or indirectly generating a detectable signal. Suitable detectable substances may include, for instance, chromogens; luminescent compounds (e.g., fluorescent, phosphorescent, etc.); radioactive compounds; visual compounds (e.g., latex or metallic particles, such as gold); liposomes or other vesicles containing signal-producing substances; enzymes and/or substrates, and so forth. For instance, some enzymes suitable for use as detectable substances are described in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable reporters may be described in U.S. Pat. No. 5,670,381 to Jou, et al. and U.S. Pat. No. 5,252,459 to Tarcha, et al., which are incorporated herein in their entirety by reference thereto for all purposes.

In some embodiments, the reporters may contain a luminescent compound that produces an optically detectable signal. The luminescent compound may be a molecule, polymer, dendrimer, particle, and so forth. For example, suitable fluorescent molecules may include, but not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis [(4,4'-carbomethoxy)-2,2'-bipyridine]2-[3-(4-methyl-2,2'-bipyridine-4-yl)propyl]-1,3-dioxolane ruthenium (II); bis(2, 2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2, 2'bipyridine)ruthenium (II); (2,2'-bipyridine)[bis-bis(1,2-diphenylphosphino)ethylene]2-[3-(4-methyl-2,2'-bipyridine-4'-yl)propyl]-1,3-dioxolane osmium (II); bis(2, 2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613, 583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, "time-resolved" luminescent detection techniques are utilized. Time-resolved detection involves exciting a luminescent compound with one or more short pulses of light, then typically waiting a certain time (e.g., between approximately 1 to 100 microseconds) after excitation before measuring the remaining the luminescent signal. In this manner, any short-lived phosphorescent or fluorescent background signals and scattered excitation radiation are eliminated. This ability to eliminate much of the background signals may result in sensitivities that are 2 to 4 orders greater than conventional fluorescence or phosphorescence. Thus, time-resolved detection is designed to reduce background signals from the emission source or from scattering processes (resulting from scattering of the excitation radiation) by taking advantage of the characteristics of certain luminescent materials.

To function effectively, time-resolved techniques generally require a relatively long emission lifetime for the luminescent compound. This is desired so that the compound emits its signal well after any short-lived background signals dissipate. Furthermore, a long luminescence lifetime makes it possible to use low-cost circuitry for time-gated measurements. For example, the detectable compounds may have a luminescence lifetime of greater than about 1 microsecond, in some embodiments greater than about 10 microseconds, in some embodiments greater than about 50 microseconds, and in some embodiments, from about 100 microseconds to about 1000 microseconds. In addition, the compound may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, one suitable type of fluorescent compound for use in time-resolved detection techniques includes lanthanide chelates of samarium (Sm (III)), dysprosium (Dy (III)), europium (Eu (III)), and terbium (Tb (III)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have exceptionally large Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent compound. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amino]methyl)-pyridine [Ref: Lovgren, T., et al.; Clin. Chem. 42, 1196–1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596–601 (1998)]. In addition to the fluorescent compounds described above, other compounds that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; U.S. Pat. No. and 5,637,509 to Hemmila, et al., which are incorporated herein in their entirety by reference thereto for all purposes.

As stated, the reporter may indirectly generate a detectable signal in some embodiments of the present invention. In such instances, the reporter may not specifically contain a detectable substance, but instead be capable of interacting with a detectable substance to generate a detection signal. For example, in some embodiments, the reporter may be a member of a specific binding pair, i.e., two different molecules where one of the molecules chemically and/or physically binds to the second molecule. Immunoreactive specific binding members may include antigens, haptens, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding members include, but are not limited to, biotin and avidin, streptavidin, neutravidin, captavidin, or an anti-biotin antibody; protein A and G; carbohydrates and lectins, complementary nucleotide sequences (including probe and capture nucleic acid sequences used in DNA hybridization assays to detect a target nucleic acid sequence); complementary peptide sequences including those formed by recombinant methods; effector and receptor molecules; hormone and hormone binding protein; enzyme cofactors and enzymes, enzyme inhibitors and enzymes; derivatives thereof, and so forth. Furthermore, specific binding pairs may include members that are analogs, derivatives, and/or fragments of the original specific binding member. When used to indirectly generate a signal, a reporter that is a member of a specific binding pair may be placed into contact with a probe conjugated with another member of the specific binding pair. Thus, the released reporter will bind to the conjugated probe, which may then be readily detected (directly or indirectly) using techniques well known to those skilled in the art.

Whether or not the reporter directly or indirectly generates a signal, it may contain particles (sometimes referred to as "beads" or "microbeads"). Among other things, particles enhance the ability of the reporter to travel through a chromatographic medium and become immobilized within a detection zone, such as described below. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex particles are labeled with a fluorescent or colored dye. Although any latex particle may be used, the latex particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. of Eugene, Oreg. In addition, commercially available examples of suitable colored, latex microparticles include carboxylated latex beads sold by Bangs Laboratories, Inc. of Fishers, Ind.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

In addition to being joined to a reporter, such as described above, the substrate is also joined to a magnetic substance. Generally, a material is considered "magnetic" or "magnetically responsive" if it is influenced by the application of a magnetic field, such as, for example, if it is attracted or repulsed or has a detectable magnetic susceptibility or induction. For instance, some examples of suitable magnetically responsive substances that may be used to impart magnetic properties include, but are not limited to, paramagnetic materials, superparamagnetic materials, ferromagnetic materials, ferrimagnetic materials, and metamagnetic materials. Specific examples are metals such as iron, nickel, cobalt, chromium, and manganese; lanthanide elements, such as neodymium, erbium; alloys, such as magnetic alloys of aluminum, nickel, cobalt, or copper; oxides, such as ferric oxide ($Fe_3O_4$), ferrous oxide ($Fe_2O_3$), chromium oxide ($CrO_2$), cobalt oxide (CoO), nickel oxide ($NiO_2$), or manganese oxide ($Mn_2O_3$); composite materials, such as ferrites; and solid solutions, such as magnetite with ferric oxide. In some embodiments of the present invention, the magnetic substance contains a magnetic particle. When utilized, the shape and/or size of the particles may vary, such as described above.

The reporter and magnetic substance may generally be joined to the substrate using any of a variety of well-known techniques. For instance, covalent attachment of a reporter and/or magnetic substance to a substrate may be accomplished using carboxylic, amino, aldehyde, bromoacetyl, iodoacetyl, thiol, epoxy or other reactive functional groups, as well as residual free radicals and radical cations, through which a coupling reaction may be accomplished. A surface functional group may also be incorporated as a functionalized co-monomer because the surface of the reporter may contain a relatively high surface concentration of polar groups. In certain cases, the reporter or magnetic substance may be capable of direct covalent bonding to a substrate without the need for further modification. It should also be understood that, besides covalent bonding, other attachment techniques, such as physical adsorption, may also be utilized in the present invention. Still other non-covalent linkage techniques may employ antibodies and/or antigens, such as secondary antibodies (e.g., avidin, streptavidin, neutravidin, and/or biotin).

One particular technique for covalently bonding a reporter and magnetic substance to a substrate will now be described in more detail. In this particular embodiment, the substrate is β-casein, the reporter is a biotin derivative, and the magnetic substance is a paramagnetic iron oxide particle. For example, the magnetic particle may be carboxylated magnetic iron oxide particles obtained from Bangs Laboratories, Inc. (Fishers, Ind.) under the name BioMag® BM570. Likewise, the reporter may be sulfosuccinimidyl-6-(biotinamido) hexanoate, which is available from Pierce Biotechnology, Inc. of Rockford, Ill. under the name EZ-Link® Sulfo-NHS-LC-Biotin. Techniques employed in making such NHS-activated biotins are believed to be described in U.S. Pat. No. 5,872,261 to Bremmer, et al., which is incorporated herein in its entirety by reference thereto for all purposes.

Figure 6:
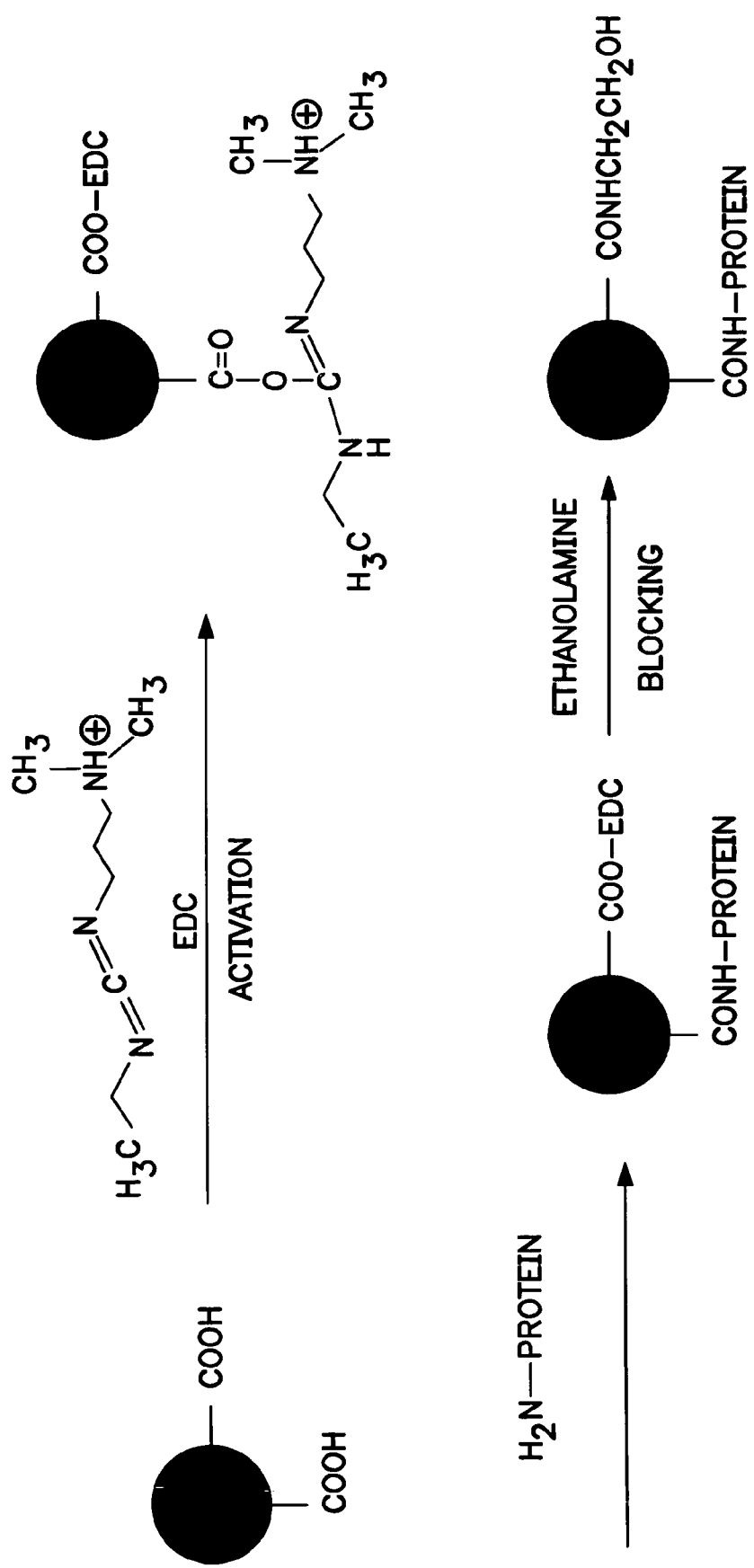
FIG. 6 is a graphical illustration of one embodiment for covalently bonding a reporter to a substrate.

To covalently conjugate the magnetic particle with β-casein, the carboxylic groups on the particle surface are first activated with a carbodiimide (e.g., ethylcarbodiimide hydrochloride (EDC)), such as shown in FIG. 6. Because protein and glycoprotein substrates (e.g., β-casein) typically possess primary amine groups ($NH_2$), such as on the side chain of lysine (K) residues and/or the N-terminus of each polypeptide, the activated carboxylic acid groups may then be reacted with the primary amine (—$NH_2$) groups of the substrate to form an amide bond. This reaction may occur in a buffer, such as phosphate-buffered saline (PBS) (e.g., pH of 7.2), 2-(N-morpholino) ethane sulfonic acid (MES) (e.g., pH of 5.3), or borate buffer (e.g., pH of 8.5). If desired, the resulting reactive complexes may then be blocked with ethanolamine, for instance, to block any remaining activated sites.

In a somewhat similar manner, the biotin-based reporter may also be covalently bonded to β-casein. For example, NHS-activated biotins may form covalent amide bonds with the primary amine groups present on the substrate (optionally in the presence of a buffer). An example of such a reaction is set forth below:

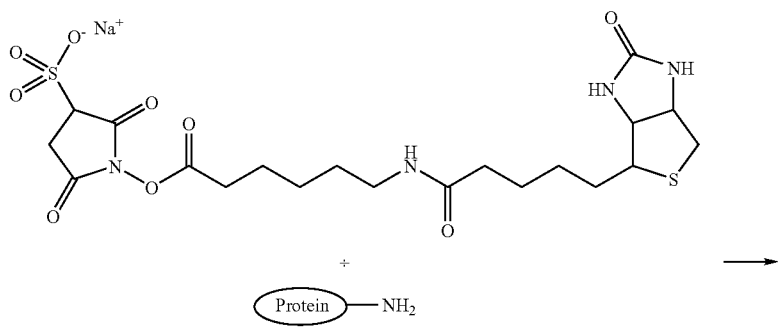

-continued

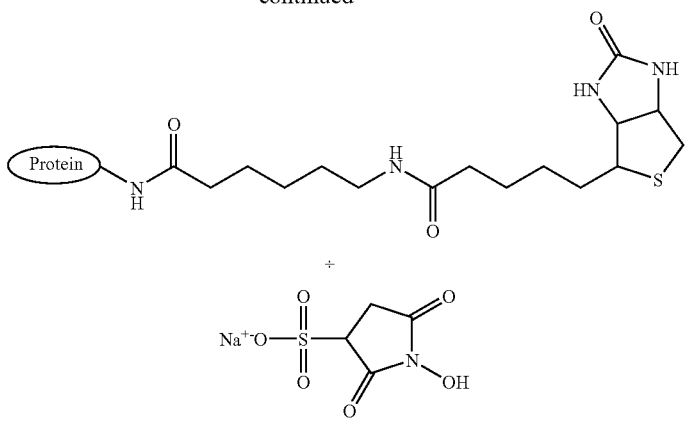

Once formed, a user may allow the test sample to incubate with the reactive complexes for a certain period of time. For example, those skilled in the art readily recognize that the time of incubation for an enzyme-catalyzed reaction depends on the activity of the enzyme of interest, which in turn depends on in part on the temperature, pH, substrate concentration, the presence of inhibitors (competitive (binds to enzyme), uncompetitive (binds to enzyme-substrate complex), or noncompetitive (binds to enzyme and/or enzyme-substrate complex)), and so forth. These factors may be selectively controlled as desired to increase or decrease the incubation time. For example, the time for incubation may be greater in some embodiments, from about 10 to about 25 minutes. Likewise, the pH may be selectively controlled to facilitate enzyme activity. For example, high levels of basic substances (e.g., amines) within a test sample may result in a pH that is too high for optimum activity of some enzymes, e.g., greater than 8. Specifically, an enzyme may possess optimum activity at a pH level of from about 3 to about 8, and in some embodiments, from about 4 to about 7. Thus, if desired, a buffer or other pH-altering compound may be employed to maintain the desired pH.

After incubation, any enzyme present within the test sample will typically cleave the substrate of at least a portion of the reactive complexes. As a result, various species may be formed, including released reporters, released magnetic substances, partially cleaved complexes (e.g., reporter-enzyme-substrate-magnetic substance), and unreacted complexes (e.g., reporter-substrate-magnetic substance). Longer incubation times and greater enzyme concentrations may result in a greater concentration of released reporters and magnetic substances in the resulting incubation mixture. Further, it should be understood that the "released" reporters and magnetic substances may or may not contain fragments of the complex depending on the nature of the substrate and enzyme. For instance, when using longer chain substrates (e.g., proteins), the released reporters and magnetic substances may contain peptide fragments from the protein substrate. On the other hand, when using shorter chain substrates (e.g., peptides), the released reporters and magnetic substances may be relatively free of such fragments.

During and/or after incubation, any released magnetic substances, partially cleaved reactive complexes, and unreacted complexes are removed from the incubation mixture using a magnetic field. A magnetic field generator, for instance, may be used to generate a magnetic field that elicits a response from the magnetic substances. Suitable magnetic field generators include, but are not limited to, permanent magnets and electromagnets. Some commercially available examples of suitable magnetic separation devices include the Dynal MPC series of separators manufactured by Dynal, Inc. of Lake Success, N.Y., which employ a permanent magnet located externally to a container holding a test medium. Still other methods for capturing magnetic substances may be described in U.S. Pat. No. 5,200,084 to Liberti, et al.; U.S. Pat. No. 5,647,994 to Tuunanen, et al.; U.S. Pat. No. 5,795,470 to Wang, et al.; and U.S. Pat. No. 6,033,574 to Siddigi, which are incorporated herein in their entirety by reference thereto for all purposes. When the magnetic substances are separated during or just after forming the incubation mixture, the mixture may be agitated to keep the magnetic substances suspended for a sufficient period of time to ensure that enzyme cleavage is substantially complete. Examples of known agitation methods include shaking, swirling, rocking, rotation, or similar manipulations of a partially filled container.

Once the magnetic substances (including partially cleaved and unreacted complexes) are removed, the remaining portion of the incubation mixture (e.g., the supernatant) may be tested for the presence of an enzyme. Generally speaking, as enzyme concentration begins to increase in the test sample, more reporters become released that are free from a magnetic substance and are thus not removed during magnetic separation. Consequently, enzyme concentration correlates to the quantity of the released reporters present in the supernatant portion of the incubation mixture. If the reporter is capable of directly generating a detection signal (e.g., luminescent compounds, colored dyes, etc.), the presence or intensity of the detection signal may simply be determined qualitatively, quantitatively, or semi-quantitatively. For example, in one embodiment, the amount of enzyme is directly proportional to the signal intensity of the released reporters in the supernatant. If desired, the signal intensity may be plotted versus the enzyme concentration for a range of known enzyme concentrations to generate an intensity curve. To determine the quantity of enzyme in an unknown test sample, the signal intensity may then be converted to enzyme concentration according to the intensity curve.

In some cases, however, it may be desired to first assay the released reporters before attempting to determine the presence or intensity of a detection signal. This may be particularly useful in situations where the reporter is only indirectly detectable (e.g., a specific binding member). Alternatively, even if the reporter is directly detectable, a subsequent assay may still enhance the sensitivity and/or accuracy of detection.

In this regard, various embodiments of an assay device that may optionally be used in the present invention to facilitate detection will now be described in more detail. Referring to FIG. 1, for instance, one embodiment of an assay device 20 is shown that contains a chromatographic medium 23 carried by a support 21. The chromatographic medium 23 may be made from any of a variety of materials through which a fluid is capable of passing, such as a fluidic channel, porous membrane, etc. For example, the chromatographic medium 23 may be a porous membrane formed from materials such as, but not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms. Although not required, the use of the chromatographic medium 23 for chemical separation may provide enhanced benefits over other conventional separation techniques, such as centrifugation. For example, the chromatographic medium 23 may simplify and reduce the costs of the resulting diagnostic test kit for many consumer applications, including those in which a disposable kit is desired.

The support 21 may be formed from any material able to carry the chromatographic medium 23. Although not required, the support 21 may be transparent so that light readily passes therethrough. In addition, it is also generally desired that the support 21 is liquid-impermeable so that fluid flowing through the medium does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. As is well known the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate structures are described in U.S. Pat. No. 5,075,077 to Durley, III, et al., which is incorporated herein in its entirety by reference thereto for all purposes.

The assay device 20 may also utilize an absorbent material 28. The absorbent material 28 generally receives fluid that has migrated through the entire chromatographic medium 23. As is well known in the art, the absorbent material 28 may assist in promoting capillary action and fluid flow through the medium 23.

In the embodiment illustrated in FIG. 1, incubation and magnetic separation are conducted before applying the test sample to the chromatographic medium 23. Thus, to initiate the assay, a user may simply apply the remaining portion of the incubation mixture (e.g., supernatant) to the porous membrane 23 through which it may then travel in the direction illustrated by arrow "L" in FIG. 1. Alternatively, the supernatant may first be applied to a sample pad 22 that is in fluid communication with the porous membrane 23. Some suitable materials that may be used to form the sample pad 22 include, but are not limited to, nitrocellulose, cellulose, porous polyethylene pads, and glass fiber filter paper. If desired, the sample pad 22 may also contain one or more assay pretreatment reagents, either diffusively or non-diffusively attached thereto. Optionally, the supernatant travels from the sample pad 22 to one or more conjugate pads (not shown) that are placed in communication with one end of the sample pad 22. The conjugate pads may be formed from a material through which the test sample is capable of passing, such as glass fibers.

Regardless, the chromatographic medium 23 defines a detection zone 31 within which the released reporters may be captured and detected. The manner in which the released reporters are captured may depend on the nature of the reporters utilized. For example, in some embodiments, a biological receptive material may be immobilized within the detection zone 31 for capturing biological reporters. Such biological receptive materials are well known in the art and may include, but are not limited to, antibodies, antigens, haptens, biotin, avidin, streptavidin, neutravidin, captavidin, protein A, protein G, carbohydrates, lectins, nucleotide sequences, peptide sequences, effector and receptor molecules, hormone and hormone binding protein, enzyme cofactors and enzymes, enzyme inhibitors and enzymes, and derivatives thereof.

For example, the released reporter may be conjugated with a specific binding member selected to have an affinity for the receptive material within the detection zone 31. The specific binding members may be conjugated to the reporters using any of a variety of well-known techniques, such as through covalent bonding and/or physical adsorption in a manner such as described above. In one particular embodiment, carboxylic groups of the reporter are activated and reacted with amino groups of an antibody to form an amide bond. In this instance, the released reporters may become immobilized within the detection zone 31 through specific binding between the antibody and a receptive material so that the signal generated by the detectable substance may be detected. For example, the reporter may contain a secondary antibody (e.g., Mouse IgG antibody ("biotin")) and the receptive material may contain another secondary antibody (such as an anti-biotin antibody, e.g., goat anti-Mouse IgG antibody), avidin (a highly cationic 66,000-dalton glycoprotein), streptavidin (a nonglycosylated 52,800-dalton protein), neutravidin (a deglysolated avidin derivative), or captavidin (a nitrated avidin derivative).

Of course, any other suitable technique for capturing and detecting the released reporters may also be used. For example, in some embodiments, non-biological receptive materials may be immobilized within the detection zone 31 for capturing released reporters. Such non-biological receptive materials may be particularly useful in capturing, for example, released reporters that contain labeled particles. For instance, in one embodiment, the receptive material is a polyelectrolyte. Polyelectrolytes may have a net positive or negative charge, as well as a net charge that is generally neutral. Some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized in the present invention, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly (styryl-b-acrylic acid), both of which are available from Polymer Source, Inc. of Dorval, Canada. Further examples of polyelectrolytes are described in more detail in U.S. Patent App. Publication No. 2003/0124739 to Song, et al., which is incorporated herein in it entirety by reference thereto for all purposes.

Although any polyelectrolyte may generally be utilized, the polyelectrolyte selected for a particular application may vary depending on the nature of the released reporters. In particular, the distributed charge of a polyelectrolyte allows it to bind to substances having an opposite charge. Thus, for example, polyelectrolytes having a net positive charge are often better equipped to bind with released reporters (e.g., dyed particles) that are negatively charged, while polyelectrolytes that have a net negative charge are often better equipped to bind to released reporters that are positively charged. Thus, in such instances, the ionic interaction between these molecules allows the required binding to occur within the second detection zone 35. Nevertheless, although ionic interaction is primarily utilized to achieve the desired binding, it has also been discovered that polyelectrolytes may bind with reporters having a similar charge.

The detection zone 31 may generally provide any number of distinct detection regions so that a user may better determine the concentration of an released reporter within a test sample. When utilized, each region may contain the same or different receptive materials. For example, the detection zone 31 may include two or more distinct detection regions (e.g., lines, dots, etc.). The use of two or more distinct detection regions may provide certain benefits, such as facilitating semi-quantitation and/or inhibiting potential false positives due to overrunning of the reactive complexes or other materials. The detection regions may be disposed in the form of lines in a direction substantially perpendicular to the flow of the test sample through the chromatographic medium 23. Likewise, in some embodiments, the detection regions may be disposed in the form of lines in a direction substantially parallel to the flow of the test sample through the medium 23.

For the embodiment shown in FIG. 1, as enzyme concentration increases in a test sample, more reporters are released and become immobilized within the detection zone 31. The increased quantity of released reporters at the detection zone 31 results in an increase in signal intensity. From this increase in signal intensity, the presence or concentration of the enzyme may be readily determined. For example, in one embodiment, the amount of enzyme is directly proportional to the signal intensity at the detection zone 31, $I_1$. If desired, the signal intensity $I_1$ may be plotted versus the enzyme concentration for a range of known enzyme concentrations to generate an intensity curve. To determine the quantity of enzyme in an unknown test sample, the signal intensity may then be converted to enzyme concentration according to the intensity curve.

It should be understood that one or more distinct regions of the detection zone 31 may exhibit the above-described relationship between signal intensity and enzyme concentration; however, each distinct region need not exhibit such a relationship. For example, in some embodiments, only one of multiple distinct regions may exhibit a signal intensity that is directly proportional to the concentration of the enzyme. The signal intensity of other distinct regions, such as those used to reduce false positives, may otherwise remain constant, or exhibit an increase and/or decrease in signal intensity. So long as at least one distinct region of the detection zone 31 satisfies the direct relationship, the signal intensity exhibited by the detection zone 31 is considered directly proportional to the enzyme concentration.

Figure 2:
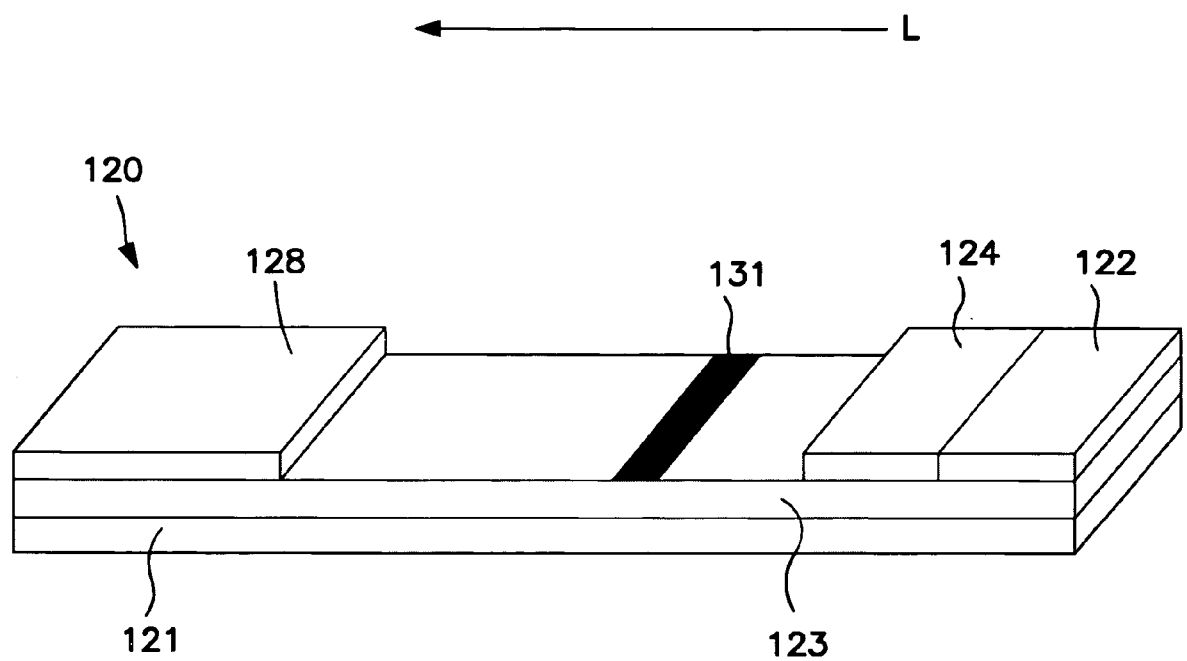
FIG. 2 is a perspective view of another embodiment of an assay device that may be used in the diagnostic test kit of the present invention.

As stated above, certain embodiments of the present invention may utilize a reporter that is not directly detectable. Thus, when released, it is generally desired that the reporter interact in some manner with a detectable substance for subsequent detection. In this regard, various embodiments of indirectly detecting the presence of a released reporter will now be described in more detail. Referring to FIG. 2, for example, an assay device 120 is shown that includes a chromatographic medium 123 positioned on a support 121, an absorbent material 128, and a sample pad 122. Because the reporters are not directly detectable, probes capable of generating a detectable signal are employed that are configured to bind to the released reporters. For example, the probes may contain a detectable substance, such as described above. The probes may also contain particles labeled or otherwise applied with the detectable substance. In some instances, it is desired to modify the probes in some manner. For example, the probes may be modified with a specific binding member to form conjugated probes that have specific affinity for the released reporters. The specific binding members may generally be conjugated to the probes using any of a variety of well-known techniques, such as through covalent bonding and/or physical adsorption in a manner such as described above. In one particular embodiment, carboxylic groups on the probe surface are activated and reacted with amino groups of the specific binding member to form an amide bond.

Although not required, the probes are typically contacted with the released reporters within the supernatant after magnetic separation. After allowing for sufficient reaction between the probes and released reporters, the entire mixture may then be applied to the assay device 120. Alternatively, the probes may be applied to the assay device 120 at a location upstream from the region in which detection is desired. For example, in one embodiment, the probes may be applied to a conjugated pad 124 that is located downstream from the sample pad 122 and upstream from any detection zones.

Regardless of its particular configuration, the assay device 120 typically includes a first detection zone 131 within which the released reporters may be captured and detected. The released reporters may be detected within the detection zone 131 utilizing a variety of assay formats. In one embodiment, for example, a "sandwich" assay format is utilized in which the released reporter is selected to have an affinity for the specific binding member of a conjugated probe. The released reporter, such as antibodies, antigens, etc., typically has two or more binding sites (e.g., epitopes). One of these binding sites becomes occupied by the specific binding member of the conjugated probe. However, the free binding site of the released reporter may subsequently bind to a receptive material immobilized within the first detection zone 131 to form a new ternary sandwich complex. Alternatively, the released reporter may be detected using direct or indirect "competitive" assay formats. In such instances, the specific binding member of the conjugated probe may be the same as or an analog of the released reporter. Thus, upon reaching the detection zone 131, the conjugated detection probes and the released reporters compete for available binding sites of the immobilized receptive material. Of course, any other assay format is also suitable for use in the present invention.

For the embodiment shown in FIG. 2, as enzyme concentration begins to increase in the test sample, more reporters are released. Thus, if a sandwich assay format is used, more reporters bind to the conjugated probes so that the amount of enzyme is directly proportional to the signal intensity at the detection zone 131. On the other hand, if a competitive assay format is used, the amount of enzyme is indirectly proportional to the signal intensity at the detection zone 131. If desired, the signal intensity may be plotted versus the enzyme concentration for a range of known enzyme concentrations to generate an intensity curve. To determine the quantity of enzyme in an unknown test sample, the signal intensity may then be converted to enzyme concentration according to the intensity curve.

Figure 3:
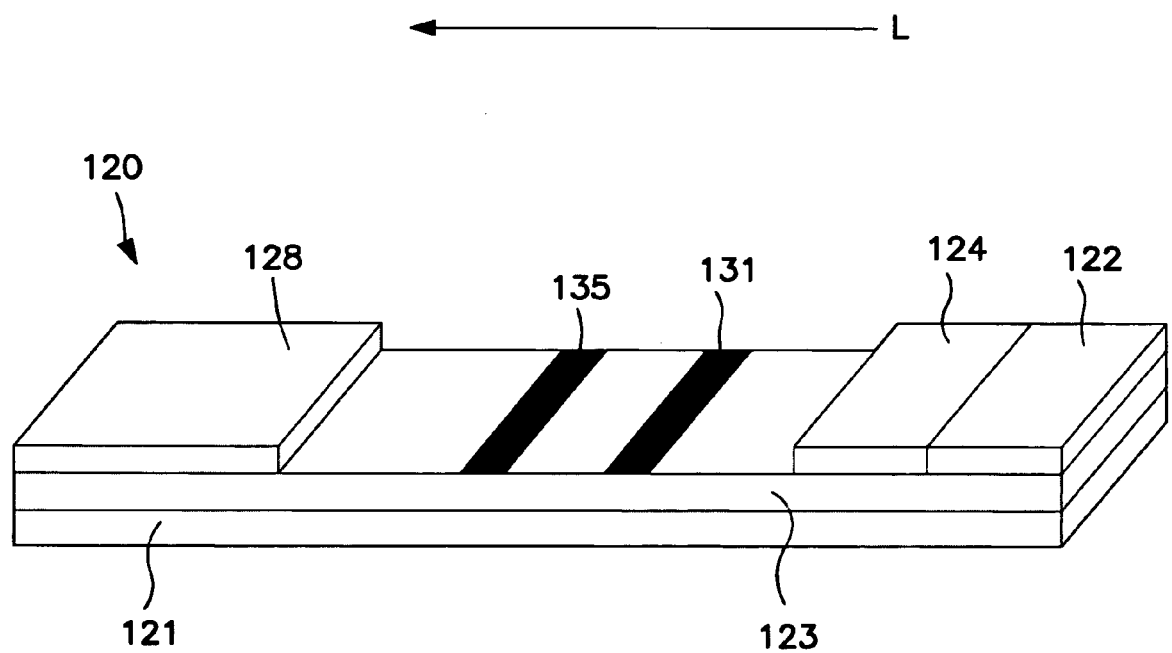
FIG. 3 is a perspective view of another embodiment of the assay device of FIG. 2.

As discussed above, an inverse relationship may exist in some circumstances between enzyme concentration and signal intensity (e.g., competitive assay formats). Because it is not always desirable to use an assay format that correlates an "increase" in enzyme concentration to a "decrease" in signal intensity (e.g. consumer applications), the present invention also provides for embodiments in which an "increase" in enzyme concentration in these embodiments may be directly correlated to an "increase" in signal intensity. For example, referring to FIG. 3, an assay device 120 is illustrated that is the same as the assay device 120 of FIG. 2, except that it also contains a second detection zone 135 positioned downstream from the detection zone 131. The second detection zone 135 may provide one or more distinct regions (e.g., line, dot, etc.), and may be positioned at any orientation relative to the flow of the test sample. A second receptive material is immobilized on the medium 123 within the second detection zone 135. The second receptive material serves as a stationary binding site for any probes that do become bound within the first detection zone 131.

The second receptive material may be a biological receptive material, a polyelectrolyte, etc. Because the second receptive material desirably binds to the probes, however, it is normally different than the first receptive material. In one embodiment, for example, in which a "direct" competitive assay is employed, the reporter contains an antigen (e.g., C-reactive protein) and the probes are dyed latex particles conjugated with the antigen. The first receptive material contains an antibody (e.g., anti-C-reactive protein (anti-CRP1) monoclonal antibody) that has a specific binding affinity for the reporter and the antigen of the conjugated probes. The second receptive material contains a polyelectrolyte that has a specific binding affinity for the probes. When present, the reporters compete with the conjugated probes for available binding sites of the first receptive material. Any remaining, unbound conjugated probes travel past the first detection zone 131 to the second detection zone 135. Because the probes have a specific affinity for the selected polyelectrolyte, they become immobilized within the second detection zone 135.

Likewise, in another embodiment in which an "indirect" competitive assay is employed, the reporter may contain a specific binding member (e.g., biotin) and the probes may be dyed particles conjugated with a complementary binding member (e.g., streptavidin) that has affinity for the reporter. The first receptive material contains a specific binding member that is the same as or an analog of the reporter, thereby having an affinity for the conjugated probes. The second receptive material contains a polyelectrolyte having binding affinity for the probes. When present, the reporter binds to the conjugated probes, thereby reducing the amount of conjugated probes otherwise available for binding to the first receptive material. Instead, those conjugated probes which are complexed to the reporter, travel past the first detection zone 131 to the second detection zone 135. Because the probes have a specific affinity for the selected polyelectrolyte, they become immobilized within the second detection zone 135.

In the competitive assay embodiments referred to above, as the concentration of the enzyme increases, the signal intensity at the second detection zone 135, $I_2$, also begins to increase due to the presence of released reporters. From this increase in signal intensity, the presence or concentration of the enzyme may be readily determined. For example, in one embodiment, the amount of enzyme is directly proportional to the signal intensity at the second detection zone 135, $I_2$. If desired, the signal intensity $I_2$ may be plotted versus the enzyme concentration for a range of known enzyme concentrations to generate an intensity curve. To determine the quantity of enzyme in an unknown test sample, the signal intensity may then be converted to enzyme concentration according to the intensity curve. It should be understood that, as discussed above with respect to the first detection zone 31 and/or 131, so long as one distinct region of the second detection zone 135 satisfies the direct relationship, the signal intensity exhibited by the second detection zone 135 is considered directly proportional to the enzyme concentration.

Also, in the embodiments referenced above, an inverse relationship may exist between the signal intensity at the detection zone 131 ($I_1$) and the second detection zone 135 ($I_2$). For example, because a predetermined amount of conjugated probes are present, the amount captured at the second detection zone 135 is inversely proportional to the amount captured at the detection zone 131. As a result of this inverse relationship, the concentration of the enzyme may, in some cases, be more effectively measured over an extended range by comparing the signal intensity at both detection zones. For example, in one embodiment, the amount of enzyme is directly proportional to the ratio of the signal intensity "$I_2$" to the signal intensity "$I_1$." Based upon the range in which this ratio falls, the general concentration range for the enzyme may be determined. If desired, the ratio of $I_2$ to $I_1$ may be plotted versus enzyme concentration for a range of known enzyme concentrations to generate an intensity curve. To determine the quantity of enzyme in an unknown test sample, the signal intensity ratio may then be converted to enzyme concentration according to the intensity curve. It should be noted that alternative mathematical relationships between $I_1$ and $I_2$ may be plotted versus the enzyme concentration to generate the intensity curve. For example, in one embodiment, the value of $I_2/(I_2+I_1)$ may be plotted versus enzyme concentration to generate the intensity curve.

Figure 4:
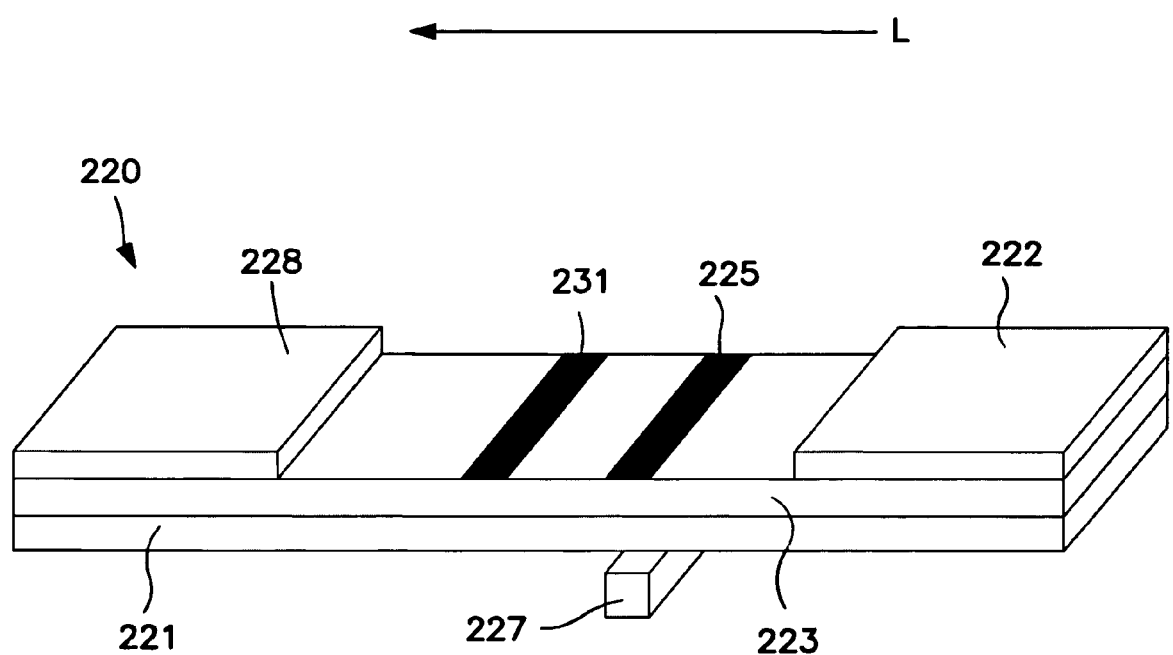
FIG. 4 is a perspective view of still another embodiment of an assay device that may be used in the diagnostic test kit of the present invention.

In the techniques described above, magnetic separation of the released magnetic substance, partially cleaved reactive complexes, and unreacted complexes generally occur prior to assaying the released reporters. In some embodiments, however, the magnetic separation step may be incorporated as part of the assaying procedure. For instance, referring to FIG. 4, one embodiment of an assay device 220 that incorporates a magnetic separation step is shown. As illustrated, the assay device 220 includes a chromatographic medium 223 carried by a support material 221, an absorbent material 228, and a sample pad 222. In this embodiment, the incubation mixture (without or without probes) is directly applied to the sample pad 222 through which it may then travel in the direction illustrated by arrow "L". A magnetic device 227 is positioned adjacent to the medium 223 at a location downstream from the point of application. Thus, when the incubation mixture flows through the medium 223, any magnetic substance (released magnetic substances, partially cleaved reactive complexes, and/or unreacted complexes) become immobilized within a separation zone 225. The reporters, having been separated from the magnetic substances, may then be assayed using a detection zone 231 and/or other detection zone(s) in a manner such as described above.

Figure 5:
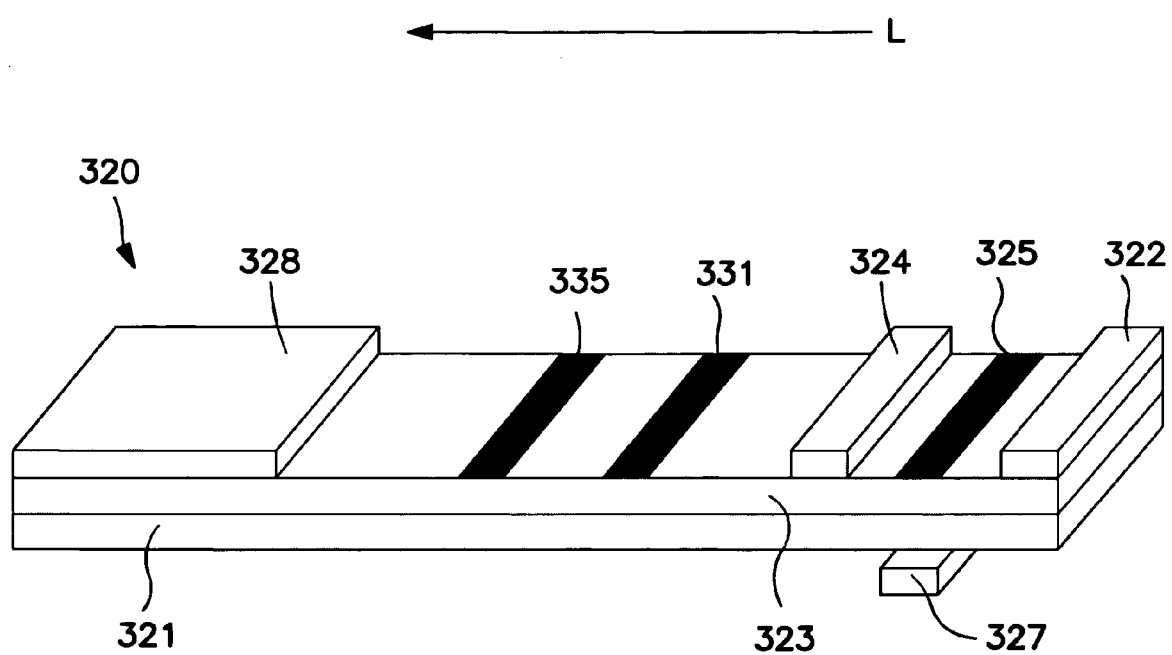
FIG. 5 is a perspective view of yet another embodiment of an assay device that may be used in the diagnostic test kit of the present invention.

Referring to FIG. 5, another embodiment of an assay device 320 that incorporates a magnetic separation step is shown. As illustrated, the assay device 320 includes a chromatographic medium 323 carried by a support material 321, an absorbent material 328, a sample pad 322, and a conjugate pad 324. In this embodiment, the incubation mixture (without or without probes) is directly applied to the sample pad 322 through which it may then travel in the direction illustrated by arrow "L". A magnetic device 327 is positioned adjacent to the medium 323 at a location downstream from the point of application (i.e., the sample pad 322) and upstream from the conjugate pad 324. Thus, when the incubation mixture flows through the medium 323, any magnetic substance (released magnetic substances, partially cleaved reactive complexes, and/or unreacted complexes) become immobilized within a separation zone 325. If desired, the magnetic device 327 may also be positioned in other locations, such as below the sample pad 322. In one embodiment, the reporters then contact conjugated probes present at the conjugate pad 324 for detection within first and second detection zones 331 and 335 in a manner such as described above.

As stated above, signal intensity may be determined qualitatively, quantitatively, and/or semi-quantitatively. In embodiments in which a quantitative result is desired, signal intensity may be determined using any of a variety of techniques known in the art. For example, in some embodiments, fluorescence detection techniques are utilized. Fluorescence detection generally utilizes wavelength filtering to isolate the emission photons from the excitation photons, and a detector that registers emission photons and produces a recordable output, usually as an electrical signal or a photographic image. One suitable fluorescence detector for use with the present invention is a FluoroLog III Spectrofluorometer, which is sold by SPEX Industries, Inc. of Edison, N.J. Another example of a suitable fluorescence detector is described in U.S. Patent Application Publication No. 2004/0043502 to Song, et al., which is incorporated herein in its entirety by reference thereto for all purposes. Still other suitable detection techniques may include, but not limited to, phosphorescence, diffraction, reflectance, transmittance, etc. An optical reader may be capable of emitting light and also registering a detection signal (e.g., transmitted or reflected light, emitted fluorescence or phosphorescence, etc.). For example, in one embodiment, a reflectance spectrophotometer or reader may be utilized to detect the presence of reporters or probes that exhibit a visual color (e.g. dyed latex microparticles). One suitable reflectance reader is described, for instance, in U.S. Patent App. Pub. No. 2003/0119202 to Kaylor, et al., which is incorporated herein in its entirety by reference thereto for all purposes.

The aforementioned detection techniques are described specifically in the context of enzymes. However, as stated, the present invention is equally suitable for detecting the presence or quantity of an enzyme inhibitor within a test sample. To detect the presence of an enzyme inhibitor within a test sample, a predetermined quantity of a corresponding enzyme may be mixed with the test sample and allowed to incubate. In the presence of a certain amount of an enzyme inhibitor, the enzyme-catalyzed reaction does not proceed at a detectable rate. Thus, the relationship between enzyme inhibitor concentration and signal intensity will be opposite to the relationship between enzyme concentration and signal intensity. For example, using FIG. 1 as an illustration, an enzyme-catalyzed reaction will not occur in the presence of a certain amount of inhibitor. Thus, all of the reactive complexes will be removed by magnetic separation and the detection zone 31 will fail to generate a detectable signal. On the other hand, as the amount of enzyme inhibitor is reduced, the enzyme causes the reporters to release from the reactive complexes as described above. The signal intensity generated at the detection zone 31 thus begins to increase due to a corresponding increase in the presence of released reporters. Accordingly, in this particular embodiment, the amount of enzyme inhibitor within the test sample is inversely proportional to the signal intensity at the detection zone 31.

It has been discovered that the diagnostic test kit of the present invention provides a relatively simple and cost-efficient method to quickly perform on-site testing of enzymes or their inhibitors. The test kit may provide a test result that is visible so that it is easily observed by the person performing the test in a prompt manner and under test conditions conducive to highly reliable and consistent test results. The diagnostic test kit is also disposable so that, if desired, it may be discarded when the test is concluded.

The present invention may be better understood with reference to the following examples.

EXAMPLE 1

β-casein was initially conjugated to magnetic particles. Specifically, 0.25 milliliters of carboxylated magnetic particles available from Bangs Laboratories, Inc. of Fishers, Ind. under the name BioMag® (0.35-micrometer particle size, 10% solids content) were washed once with phosphate-buffered saline (PBS) (Polysciences, Inc. of Warrington, Pa.) and then suspended in 1 milliliter of PBS. 28.8 milligrams of carbodiimide (Polysciences, Inc.) in 1 milliliter of PBS was added and the resulting mixture was shaken for 30 minutes. The particles were washed twice with a borate buffer (Polysciences, Inc.), and then suspended in 1 milliliter of borate buffer. 2 milligrams of β-casein (Sigma-Aldrich Chemical Co., Inc. of St. Louis, Mo.) was added and the mixture was shaken overnight at room temperature. The particles were washed once with the borate buffer and then re-suspended in 500 microliters of borate buffer. 1 milliliter of ethanolamine solution (0.1 molar, Polysciences, Inc.) was added to the particles and shaken for 30 minutes. The particles were then washed five times with water and suspended in 2 milliliters of borate buffer.

Upon formation, the conjugated magnetic particles (hereinafter "Mp-casein") were then biotinylated. Specifically, 4 milligrams of the Mp-casein particles in 330 microliters of borate buffer were mixed with 1 milligram of EZ-Link® Sulfo-NHS-LC-Biotin (Pierce Biotechnology, Inc. of Rockford, Ill.) in 200 microliters of borate buffer. The mixture was shaken overnight and then washed five times with water. The washed particles were suspended in 1 milliliter of tris buffer (pH of 7.4, 20 millimolar). The biotinylated, conjugated magnetic particles are hereinafter referred to as "Mp-casein-B."

EXAMPLE 2

Biotin was conjugated to β-casein. Specifically, 10 milligrams of β-casein in 1 milliliter borate buffer was mixed with 5 milligrams of EZ-Link® Sulfo-NHS-LC-Biotin (Pierce Biotechnology, Inc.) in 1 microliter of borate buffer (Polysciences, Inc.). The mixture was shaken overnight and then dialyzed five times with water using a Slide-A-lyzer dialysis cassette, 3,500 MWCO (Pierce Biotechnology, Inc.). The dialyzed sample was diluted with water to a total volume of 5 milliliters. The biotinylated β-casein is hereinafter referred to as "casein-B".

EXAMPLE 3

Biotin was conjugated to bovine serum albumin (BSA, SeraCare, Inc. of Oceanside, Calif.). 500 milligrams of BSA in 9 milliliters of borate buffer were mixed with 300 milligrams of EZ-Link® Sulfo-NHS-LC-Biotin (Pierce Biotechnology, Inc.) in 1 microliter of borate buffer. The mixture was shaken overnight and then dialyzed five times with water using a Slide-A-lyzer dialysis cassette, 3,500 MWCO (Pierce Biotechnology, Inc.). The dialyzed sample was diluted with water to a concentration of 50 milligrams per milliliter. The biotinylated BSA is hereinafter referred to as "BSA-B".

EXAMPLE 4

The ability to detect the presence of an enzyme in accordance with the present invention was demonstrated. Initially, one end of a nitrocellulose porous membrane (HF 12002 from Millipore, Inc.) was laminated with a cellulosic wicking pad (Millipore, Inc.). The "BSA-B" of Example 3 (2 milligrams per milliliter) was striped onto the membrane to form a detection zone. The laminated card was dried at 37° C. for 1 hour and then cut into 4-millimeter wide assay devices.

25 microliters of the "Mp-casein-B" of Example 1 (4 milligrams per milliliter) and 75 microliters of tris buffer (pH of 7.4) were added to each of two wells (one sample well and one control well) present on a microtiter plate. 5 microliters of an active protease from Bacillus polymyxa (20 milligrams/milliliter), a metalloenzyme available from Sigma-Aldrich Chemical Co., Inc., was added to the sample well. Further, 5 microliters of a deactivated protease was added to the control well. The deactivated protease was obtained by boiling the active protease for 5 minutes. The mixtures in each well were allowed to react for 20 minutes.

After incubation, the magnetic particles in each sample were removed by a magnet separator obtained from Dynal Biotech Worldwide of Oslo, Norway. 20 microliters of supernatant from each sample was then transferred to a well containing 20 microliters of Tween 20 (2%, Sigma-Aldrich Chemical Co., Inc.) and 1 microliter of blue particles conjugated with streptavidin (1%, obtained from Bangs Laboratories, Inc.).

The assay device samples were then inserted into each respective well to initiate the test. After allowing the assay to develop for 10 minutes, the color intensity of the detection zone was observed. Specifically, a strong blue line was observed on the assay device inserted into the control well, while no blue line was observed on the assay device inserted into the sample well. Thus, the signal intensity exhibited by the detection zone decreased in the presence of the enzyme.

EXAMPLE 5

The ability to detect the presence of an enzyme in accordance with the present invention was demonstrated. Initially, one end of a nitrocellulose porous membrane (HF 12002 from Millipore, Inc.) was laminated with a cellulosic wicking pad (from Millipore, Inc.). The "casein-B" of Example 2 (2 milligrams per milliliter of water) was striped onto the membrane to form a first detection zone. A second detection zone was also formed by striping the membrane with Goldline™ (a polylysine solution available from British Biocell International). The laminated card was dried at 37° C. for 1 hour and then cut into 4-millimeter wide assay devices.

Six samples (designated Samples 1–6) were then provided that contained 50 microliters of the "MP-casein-B" of Example 1 (4 milligrams/milliliter). Each sample was incubated for 20 minutes with different amounts of an active protease from Bacillus polymyxa, a metalloenzyme available from Sigma-Aldrich Chemical Co., Inc. Specifically, the amount of active protease in Samples 1–6 ranged from 0.0, 0.2, 1.0, 2.0, 10 and 20 micrograms, respectively. For Sample 1 (control sample), 20 micrograms of deactivated protease (obtained by boiling for 30 minutes) was also added. The magnetic particles were then removed by a magnetic separator obtained from Dynal Biotech Worldwide of Oslo, Norway. 20 microliters of the supernatant of each sample was then transferred to a well containing 20 microliters of Tween 20 (1%, Sigma-Aldrich Chemical Co., Inc.) and 1 microliter of streptavidin-coated blue particles (1%, Bangs Laboratories, Inc.).

The assay device samples were then inserted into each respective well to initiate the test. After allowing the assay to develop for 10 minutes, the color intensity of each detection zone was observed. The qualitative results are set forth below in Table 1.

TABLE 1

| Qualitative Color Intensity for Detection Zones | | |
| --- | --- | --- |
| Sample | First Detection Zone | Second Detection Zone |
| 1 | Strong | None |
| 2 | Strong | Medium |
| 3 | Medium | Medium |
| 4 | Weak | Strong |
| 5 | Weak | Strong |
| 6 | None | Strong |

As indicated, the signal intensity exhibited by the first detection zone decreased in the presence of the enzyme, while the signal intensity exhibited by the second detection zone increased in the presence of the enzyme.

EXAMPLE 6

The ability to detect the presence of an enzyme in accordance with the present invention was demonstrated. Initially, one end of a nitrocellulose porous membrane (HF 12002 from Millipore, Inc.) was laminated with a cellulosic wicking pad (from Millipore, Inc.). A first detection zone was formed by striping two lines of the "casein-B" of Example 2 (2 milligram per milliliter of water) onto the membrane. A second detection zone was also formed by striping the membrane with Goldline™ (a polylysine solution available from British Biocell International). The laminated card was dried at 37° C. for 1 hour and then cut into 4-millimeter wide assay devices.

Six samples (designated Samples 1–6) were then provided that contained 20 microliters of the "MP-casein-B" formed in Example 1 (4 milligrams/milliliter). Each sample was incubated for 20 minutes with different amounts of an active protease from *Bacillus polymyxa*, a metalloenzyme available from Sigma-Aldrich Chemical Co., Inc. Specifically, the amount of active protease in Samples 1–6 ranged from 0.0, 0.02, 0.10, 0.20, 1.0, and 4.0 micrograms, respectively. For sample 1 (control sample), 200 micrograms of deactivated protease (obtained by boiling for 30 minutes) was also added. The total volume of each sample was 60 microliters. The magnetic particles were then removed by a magnetic separator obtained from Dynal Biotech Worldwide of Oslo, Norway. 20 microliters of the supernatant of each sample was then transferred to a well containing 20 microliters of Tween 20 (1%, Sigma-Aldrich Chemical Co., Inc.) and 1 microliter of streptavidin-coated blue particles (1%, obtained from Bangs Laboratories, Inc.).

The assay device samples were then inserted into each respective well to initiate the test. After allowing the assay to develop for 10 minutes, the color intensity of each detection zone was observed. The qualitative results are set forth below in Table 2.

TABLE 2

Qualitative Color Intensity for Detection Zones

| Sample | First Detection Zone (First Line) | First Detection Zone (Second Line) | Second Detection Zone |
| --- | --- | --- | --- |
| 1 | Strong | None | None |
| 2 | Medium | None | Medium |
| 3 | Medium | None | Medium |
| 4 | Weak | None | Strong |
| 5 | Weak | None | Strong |
| 6 | None | None | Strong |

As indicated, the signal intensity exhibited by the first line of the first detection zone decreased in the presence of the enzyme, while the signal intensity exhibited by the second detection zone increased in the presence of the enzyme.

EXAMPLE 7

The ability to detect the presence of an enzyme in accordance with the present invention was demonstrated. Initially, one end of a nitrocellulose porous membrane (HF 12002 from Millipore, Inc.) was laminated with a cellulosic wicking pad (from Millipore, Inc.). The "casein-B" of Example 2 (2 milligram per milliliter of water) was striped onto the membrane to form a first detection zone. A second detection zone was also formed by striping the membrane with Goldline™ (a polylysine solution available from British Biocell International). The card was dried at 37° C. for 1 hour.

A conjugate pad was prepared by soaking a 10-centimeter long glass fiber pad (Millipore Inc.) with 50 microliters of streptavidin-coated blue particles (1%, obtained from Bangs Laboratories, Inc. of Fishers, Ind.), 200 microliters of sucrose (20%, Sigma-Aldrich Chemical Co., Inc.), 100 microliters of Tween 20, and 250 microliters of tris buffer. The soaked glass fiber pad was then dried at 37° C. for 2 hours. The dried conjugate pad was laminated to the other end of the membrane. Then, a cellulose sample pad (Millipore Inc.) was laminated to an end of the conjugate pad. The laminated full card was then cut into 4-millimeter wide assay devices.

Six samples (designated Samples 1–6) were then provided that contained 20 microliters of the "MP-casein-B" of Example 1 (4 milligrams/milliliter). Each sample was incubated for 20 minutes with different amounts of an active protease from *Bacillus polymyxa*, a metalloenzyme available from Sigma-Aldrich Chemical Co., Inc. Specifically, the amount of active protease in Samples 1–6 ranged from 0.0, 0.02, 0.10, 0.20, 1.0 and 4.0 micrograms, respectively. For Sample 1 (control sample), 20 micrograms of deactivated protease (obtained by boiling for 30 minutes) was also added.

The assay device samples were then laid on a sheet available from Pechiney Plastic Packaging, Inc. of Chicago, Ill. under the name Parafilm®, and a magnetic strip was positioned below the sample pad of each device. Each respective sample was then transferred to the sample pad of each device to initiate the test. After allowing the assay to develop for 10 minutes, the color intensity of each detection zone was observed. The qualitative results are set forth below in Table 3.

TABLE 3

Qualitative Color Intensity for Detection Zones

| Sample | First Detection Zone | Second Detection Zone |
| --- | --- | --- |
| 1 | Strong | None |
| 2 | Strong | None |
| 3 | Strong | None |
| 4 | Medium | Weak |
| 5 | Medium | Medium |
| 6 | Weak | Strong |

As indicated, the signal intensity exhibited by the first detection zone decreased in the presence of the enzyme, while the signal intensity exhibited by the second detection zone increased in the presence of the enzyme.

EXAMPLE 8

The ability to detect the presence of an enzyme in accordance with the present invention was demonstrated. Initially, one end of a nitrocellulose porous membrane (HF 12002 from Millipore, Inc.) was laminated with a cellulosic wicking pad (from Millipore, Inc.) and the other end with a cellulose sample pad. A detection zone was formed by striping the membrane with Goldline™ (a polylysine solution available from British Biocell International). The laminated card was dried at 37° C. for 1 hour and then cut into 4-millimeter wide assay devices.

150 micrograms of streptavidin-coated blue particles (SA-BP, Bang's Laboratories, Inc. of Fishers, Ind.) were partially blocked by 20 microliters of biotin (2.5 micrograms per milliliter, obtained from Sigma-Aldrich Chemical Co., Inc.) by incubating the mixture for 20 minutes. 40 microliters of the above partially blocked streptavidin-coated blue particles were mixed with 30 microliters of the "MP-casein-B" of Example 1 (4 milligrams per milliliter) in 200 microliters of tris buffer for 20 minutes. The particles were then washed twice by tris buffer and then suspended in 100 microliters of tris buffer with 1% Tween 20 (Sigma-Aldrich Chemical Co., Inc.). The suspended particles were divided equally into two portions, with each portion being added to one well (one sample well and one control well) present on a microtiter plate. 5 microliters of an active protease from *Bacillus polymyxa* (20 milligrams/milliliter), a metalloenzyme available from Sigma-Aldrich Chemical Co., Inc., was added to the sample well. Further, 5 microliters of a deactivated protease was added to the control well. The deactivated protease was obtained by boiling the active protease for 5 minutes. The mixtures in each well were allowed to react for 20 minutes.

The assay device samples were then laid on a sheet available from Pechiney Plastic Packaging, Inc. of Chicago, Ill. under the name Parafilm®, and a magnetic strip was positioned below the sample pad of each device. Each respective sample was then transferred to the sample pad of each device to initiate the test. After allowing the assay to develop for 10 minutes, the color intensity of each detection zone was observed. Specifically, a strong blue line was observed on the assay device applied with the sample with active protease, while no blue line was observed on the assay device applied with the control sample.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting an enzyme, or an inhibitor thereof, within a test sample, the method comprising:
    contacting a test sample with a plurality of reactive complexes to form an incubation mixture, the reactive complexes each comprising a substrate joined to a reporter and magnetically responsive substance, wherein the substrate is cleavable by an enzyme to release the reporter, the released reporter being capable of directly or indirectly generating a detection signal;
    subjecting the incubation mixture to a magnetic field to separate a first portion containing the magnetically responsive substance from a second portion;
    contacting the second portion with a detection zone that is defined by a chromatographic medium, wherein a receptive material is immobilized within the detection zone that is capable of binding to the released reporter or a complex thereof; and
    determining the presence or intensity of the detection signal within the detection zone.

2. The method of claim 1, wherein the enzyme is a hydrolase.

3. The method of claim 2, wherein the hydrolase is a protease or peptidase.

4. The method of claim 1, wherein the substrate is a protein, glycoprotein, peptide, nucleic acid, carbohydrate, lipid, ester, or derivative thereof.

5. The method of claim 4, wherein the substrate is casein, albumin, hemoglobin, myoglobin, keratin, gelatin, insulin, proteoglycan, fibronectin, laminin, collagen, elastin, or a derivative thereof.

6. The method of claim 1, wherein the magnetically responsive substance includes a magnetically responsive particle.

7. The method of claim 6, wherein the magnetically responsive particle includes a metal or metal oxide.

8. The method of claim 1, wherein the reporter comprises a detectable substance that is capable of directly generating the detection signal.

9. The method of claim 1, wherein the reporter comprises a specific binding member.

10. The method of claim 1, further comprising contacting the second portion with probes conjugated with a specific binding member, the probes further comprising a detectable substance that is capable of directly generating the detection signal.

11. The method of claim 10, wherein a specific binding member of the probes has affinity for the specific binding member of the reporter.

12. The method of claim 10, wherein a specific binding member of the probes is the same as or an analog of the specific binding member of the reporter.

13. The method of claim 1, wherein the magnetic field is supplied by a magnetic device positioned adjacent to the chromatographic medium, wherein separation of the first portion from the second portion results in the immobilization of the magnetically responsive substance within a separation zone.

14. The method of claim 13, wherein the separation zone is positioned upstream from the detection zone.

15. The method of claim 14, wherein the separation zone is positioned downstream from the location where the second portion is applied.

16. The method of claim 1, wherein the chromatographic medium is a porous membrane.

17. The method of claim 1, wherein the amount of an enzyme within the test sample is directly proportional to the intensity of the detection signal.

18. The method of claim 1, wherein the amount of an enzyme within the test sample is inversely proportional to the intensity of the detection signal.

19. The method of claim 1, wherein the amount of an enzyme inhibitor within the test sample is directly proportional to the intensity of the detection signal.

20. The method of claim 1, wherein the amount of an enzyme inhibitor within the test sample is inversely proportional to the intensity of the detection signal.

21. The method of claim 1, wherein the chromatographic medium further comprises a second detection zone within which a second detection signal is capable of being generated.

22. The method of claim 21, wherein a second receptive material is immobilized within the second detection zone that is capable of binding to probes or complexes thereof, wherein the probes comprise a detectable substance capable of directly generating the second detection signal.

* * * * *